(12) United States Patent
Quartararo

(10) Patent No.: US 6,497,682 B1
(45) Date of Patent: Dec. 24, 2002

(54) INFECTION PREVENTING DEVICE, AND AN INTRODUCER PROVIDED THEREWITH

(76) Inventor: Peter Quartararo, 320 E. 65th St., New York, NY (US) 10021

( * ) Notice: Subject to any disclaimer, the term of this patent is extended or adjusted under 35 U.S.C. 154(b) by 63 days.

(21) Appl. No.: 09/637,204

(22) Filed: Aug. 14, 2000

(51) Int. Cl.[7] .................................................. A61M 5/32
(52) U.S. Cl. .................. 604/174; 604/177; 128/DIG. 26
(58) Field of Search ................................. 604/174, 177, 604/178, 180, 122; 128/DIG. 26, DIG. 6

(56) References Cited

U.S. PATENT DOCUMENTS

| | | | | |
|---|---|---|---|---|
| 4,516,968 A | * | 5/1985 | Marshall et al. ............... | 604/74 |
| 4,755,173 A | * | 7/1988 | Konopka et al. ............. | 604/167 |
| 4,767,411 A | * | 8/1988 | Edmunds ..................... | 604/180 |
| 4,988,341 A | * | 1/1991 | Columbus et al. ........... | 604/306 |
| 5,207,652 A | * | 5/1993 | Kay ............................. | 604/180 |
| 5,776,106 A | * | 7/1998 | Matyas ........................ | 604/180 |
| 5,885,254 A | * | 3/1999 | Matyas ........................ | 604/180 |
| 6,147,135 A | * | 11/2000 | Yuan et al. ................... | 523/105 |

FOREIGN PATENT DOCUMENTS

EP             0319764 A2 *  6/1989  ............ A61M/1/00

* cited by examiner

*Primary Examiner*—Denise L. Esquivel
*Assistant Examiner*—Marc Norman
(74) *Attorney, Agent, or Firm*—I. Zborovsky

(57) ABSTRACT

A device for preventing infections during introduction of a fluid into a body, has an element which is formed so as to surround an introducer over its periphery and extend over a part of its elongation, so that when the introducer is introduced through an opening into the body the element completely covers an area of the opening, the element being composed of a material which is biocompatible and does not cause growth of germs, bacteria, and the like.

10 Claims, 2 Drawing Sheets

INFECTION PREVENTING DEVICE, AND AN INTRODUCER PROVIDED THEREWITH

BACKGROUND OF THE INVENTION

The present invention relates to an infection preventing device and to an introducer provided with such a device.

In the medical practice often various fluids are often introduced into a patient's body such as for example blood, nutrient solution, etc. One, of the grave problems during such introduction of fluids is a danger of contamination since the introducer pierces the skin and tissues of a patient's body and producers an easy entry for bacteria, germs, etc. which cause various infections. It is therefore believed to be clear that prevention of such infections is of exceptional importance for successful treatment of patients.

SUMMARY OF THE INVENTION

Accordingly, it is an object of the present invention to provide an infection preventing device which can be used during introduction of fluids into a patient's body and efficiently protects the produced inlet from penetration of germs, bacteria, etc. with resulting infection.

In keeping with these objects and with others which will become apparent hereinafter, one feature of present invention resides, briefly stated in a device for preventing infections during introducing fluids in a body, which includes an element which is adapted to surround an introducer substantially over its periphery and extend transversely from the introducer so as to cover an area of an opening produced during introduction of a fluid by the introducer, wherein the element is composed of a material which is biocompatible, does not promote growth of bacteria, germs, etc. and prevents penetration of bacteria, germs, etc. through the opening into the body.

In accordance With another feature of present invention an introducer for introducing fluids into the body is provided, which has an introducing body with which a fluid can be introduced into the body and a device for preventing infections which has during introducing fluids in a body, which includes an element which is adapted to surround an introducer substantially over its periphery and extend transversely from the introducer so as to cover an area of an opening produced during introduction of a fluid by the introducer, wherein the element is composed of a material which is biocompatible, does not promote growth of bacteria, germs, etc. and prevents penetration of bacteria, germs, etc. through the opening into the body.

When the device and the introducer with the device are designed in accordance with the present invention, infections which are caused by insertion of an introducer for introducing fluids into the body are reliably prevented.

The novel features which are considered as characteristic for the present invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENTS

Figure 1:
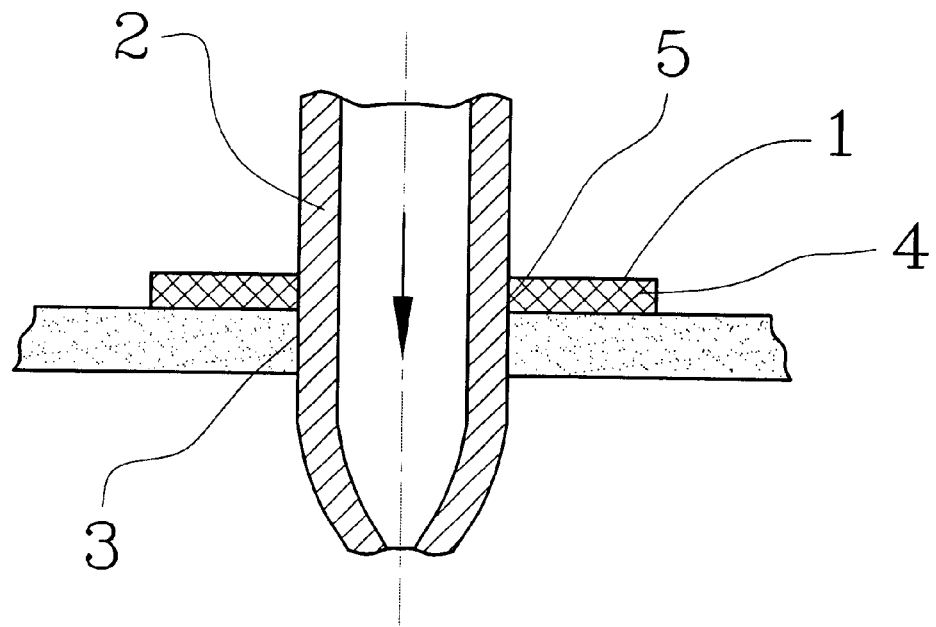
FIG. 1 is a view schematically showing an infection preventing device in accordance with the present invention.

A device for preventing infections during introduction of fluids into a body, such as during introduction of blood, nutrient solution, etc., is formed as an element 1 which is adapted to surround an introducer 2 over its periphery and extend substantially transversely to the introducer. The element 1 has a transverse dimension which is greater than the transverse dimension of the introducer 2, so that when the introducer 2 is introduced into the body through a produced opening 3, the element 1 reliably covers the area of the opening 3. In the shown embodiment the element 1 is formed as a disk which has a disk shaped body 4 and a central opening 5 which surrounds the introducer 2.

In accordance with the present invention, the element 1 is composed of a material which is biocompatible, which does not promote growth of bacteria, germs, etc., and which in some cases inhibits bacteria, germs, etc. Such a material can be, for example, a material based on polyphosphazens. For example, the material can be a mixture of high-molecular polyphosphazens such as poly-[bis-(trifluoroetoxy) phosphazens] with a molecular mass 1–1.5 million and molecular mass 1.5–2.7 million in a quantitative ratio correspondingly (0.1–5.0):(95.0–99.0).

The material can be produced by taking a molten poly-poly-[bis-(trifluoroetoxy)phosphazens] with a molecular mass 1.5–2.7 million, and adding 1.5–5.0 mass % of poly-[bis-(trifluoroetoxy)phosphazens] with a molecular mass 1–1.5 million. The obtained mixture is formed or extruded at a temperature of approximately 245–250° C. Also, other methods are possible as well.

The element produced from this material has a strong antimicrobial action during all time of contact of the element with a body of a patient.

When the introducer 2, such as a syringe, a hollow needle, etc., is introduced into the body through the skin and underlying tissues with formation of the opening 3, the element 1 reliably protects the area surrounding the opening 3 from penetration of germs, bacteria, etc. and therefore prevents infections.

Figure 2:
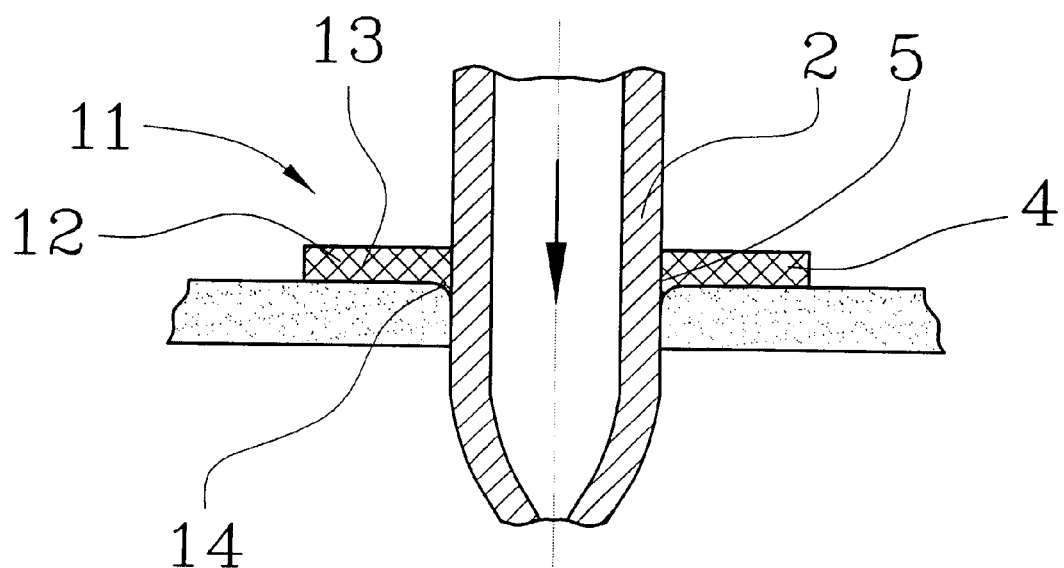
FIG. 2 is a view showing another embodiment of the infection preventing device of the present invention.

In accordance with another embodiment shown in FIG. 2 the device has an element 11 which is also composed of the material which is biocompatible, prevents growth of germs, bacteria, etc., and in some cases inhibits this growth. At the same time the device is formed somewhat differently. In particular, it has a disk shaped part 12 with a central hole 13 and a projection 14 extending in an axial direction. The projection 14, during use of the introducer with the element 11, is forcibly introduced into the skin and underlying tissues to increase the reliability of blocking any penetration of germs, bacteria, etc. The projection 14 can be slightly rounded and reducing in a diameter in an introducing direction so as to eventually reach the diameter of the outer surface of the introducer as shown in the drawings.

Figure 3:
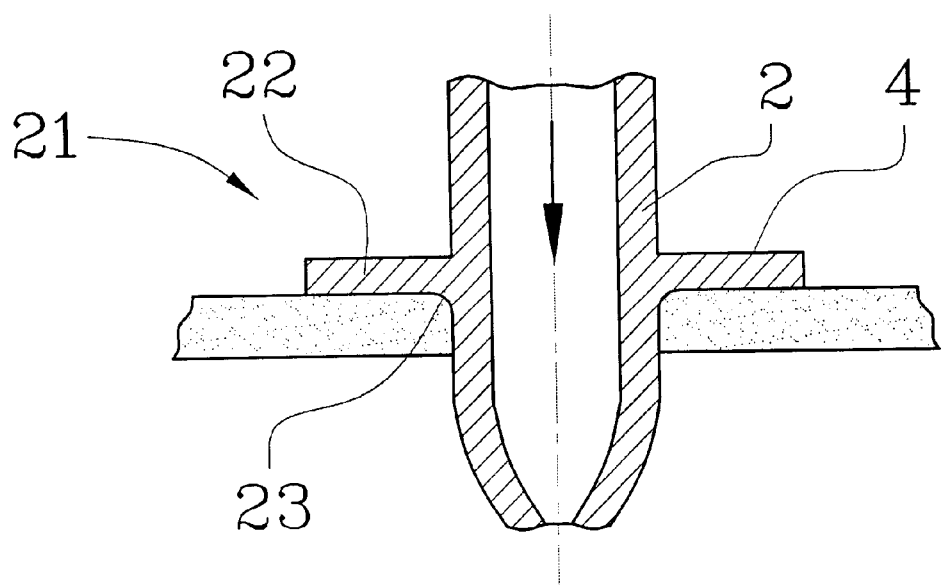
FIG. 3 is a view showing an introducer with the inventive infection preventing device.

While in the embodiment shown in FIGS. 1 and 2 the device for preventing infections during introduction of fluids into the body is formed as a separate element, the device can be also formed as an integral part of the introducer as shown in FIG. 3. Here the introducer is identified again with reference numeral 2. The device includes an element 21 which is formed as a disk 22 integral with the outer surface of the introducer 2. It can be also provided with a projection 23.

Figure 4:
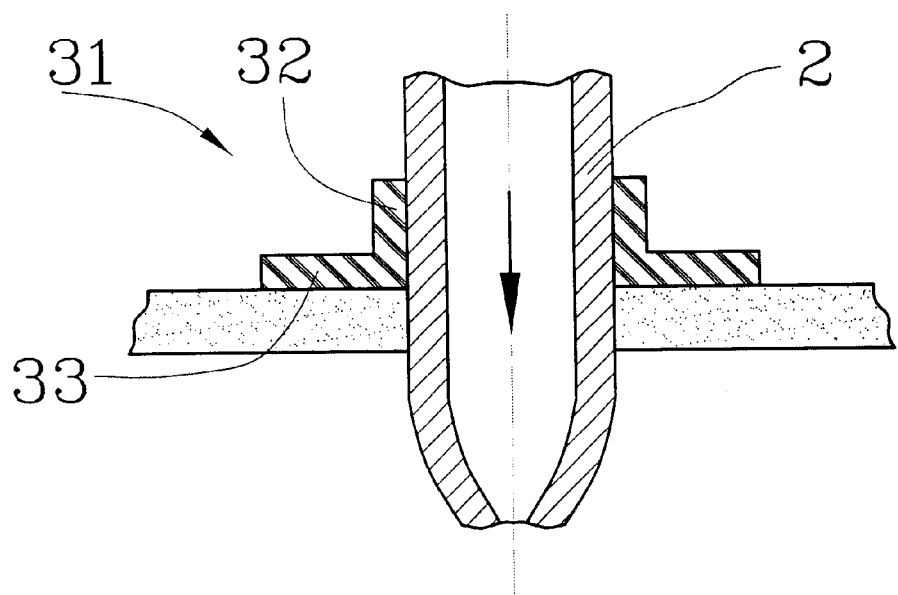
FIG. 4 view showing a further embodiment of the present invention.

In the embodiment of FIG. 4 an element 31 is formed as a sleeve which is fittable onto the introducer 2 and has a sleeve portion 32 and a disk portion 33. The element 1, 11, 21, 31 can be completely composed of the biocompatible infection preventing material, or can have a core of another material (polymer, etc.) and an outer layer of the biocompatible infection.

It will be understood that each of the elements described above, or two or more together, may also find a useful application in other types of constructions differing from the types described above.

While the invention has been illustrated and described as embodied in infection preventing device, and an introducer provided therewith, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

What is claimed is:

1. A device for preventing infections during introduction of a fluid into a body, comprising an element which is formed so as to surround an introducer over its periphery and extend over a part of its elongation, so that when the introducer is introduced through an opening into the body the element completely covers an area of the opening, said element being composed of a material which is biocompatible and does not cause growth of germs, bacteria, and the like, said element having a core composed of another material and a coating composed of said first mentioned material.

2. A device as defined in claim 1, wherein said element is disk shaped and has a central hole with which it is fittable on the introducer.

3. A device as defined in claim 1, wherein said element is sleeve-shaped and has a sleeve portion and a disk portion.

4. An introducer for introducing fluids into a body, comprising an introducing part with which a fluid can be introduced into the body; and a device for preventing infections associated with said introducing part, said device including an element which is formed so as to surround said introducing part over its periphery and extend over a part of its elongation, so that when said introducing part is introduced through an opening into the body the element completely covers an area of the opening, said element being composed of a material which is biocompatible and does not cause growth of germs, bacteria, and the like, said element having a core composed of another material and a coating composed of said first mentioned material.

5. An introducer as defined in claim 4, wherein said element is disk shaped and has a central hole with which it is fittable on the introducer.

6. An introducer as defined in claim 4, wherein said material is a mixture of high-molecular polyphosphazens consisting of poly-[bis-(trifluoroetoxy)phosphazens] with a molecular mass 1–1.5 million and molecular mass 1.5–2.7 million in a quantitative ratio correspondingly (0.15.0): (95.0–99.0).

7. An introducer as defined in claim 4, wherein said element is sleeve-shaped and has a sleeve portion and a disk portion.

8. A device for preventing infections during introduction of a fluid into a body, comprising an element which is formed so as to surround an introducer over its periphery and extend over a part of its elongation, so that when the introducer is introduced through an opening into the body the element completely covers an area of the opening, said element being composed of a material which is biocompatible and does not cause growth of germs, bacteria, and the like, said element having a projection extending in an axial direction and having a diameter reducing from an outer diameter of said projection in an introducing direction.

9. An introducer for introducing fluids into a body, comprising an introducing part with which a fluid can be introduced into the body; and a device for preventing infections associated with said introducing part, said device including an element which is formed so as to surround said introducing part over its periphery and extend over a part of its elongation, so that when said introducing part is introduced through an opening into the body the element completely covers an area of the opening, said element being composed of a material which is biocompatible and does not cause growth of germs, bacteria, and the like, said element having a projection extending in an axial direction and having a diameter reducing from an outer diameter of said projection to an outer diameter of said introducing part in an introducing direction.

10. An introducer for introducing fluids into a body, comprising an introducing part with which a fluid can be introduced into the body; and a device for preventing infections associated with said introducing part, said device including an element which is formed so as to surround said introducing part over its periphery and extend over a part of its elongation, so that when said introducing part is introduced through an opening into the body the element completely covers an area of the opening, said element being composed of a material which is biocompatible and does not cause growth of germs, bacteria, and the like, said element being formed integral of one piece with said introducing part.

* * * * *